United States Patent

Okinishi et al.

[11] Patent Number: 5,894,337
[45] Date of Patent: Apr. 13, 1999

[54] EYE FUNDUS EXAMINING APPARATUS

[75] Inventors: Satoru Okinishi, Utsunomiya; Shinya Tanaka, Tokyo; Yasuyuki Numajiri, Kawasaki; Toshiaki Okumura, Yokohama; Shigeaki Ono; Hiroshi Itoh, both of Utsunomiya; Tomoyuki Iwanaga, Yokohama, all of Japan

[73] Assignee: Canon Kabushiki Kaisha, Tokyo, Japan, JPX

[21] Appl. No.: 08/921,356

[22] Filed: Aug. 29, 1997

[30] Foreign Application Priority Data

Sep. 3, 1996 [JP] Japan .................... 8-252326

[51] Int. Cl.$^6$ .................................. A61B 3/00
[52] U.S. Cl. .................................. 351/205
[58] Field of Search .................... 351/205, 206, 351/207, 208, 222, 214, 215, 246

[56] References Cited

U.S. PATENT DOCUMENTS

| | | |
|---|---|---|
| 4,830,483 | 5/1989 | Kohayakawa et al. |
| 4,866,243 | 9/1989 | Sakane et al. |
| 5,270,749 | 12/1993 | Okumura |
| 5,446,509 | 8/1995 | Okinishi |
| 5,455,644 | 10/1995 | Yazawa et al. |
| 5,615,683 | 4/1997 | Toge et al. |
| 5,757,463 | 5/1998 | Kohayakawa ............ 351/214 |
| 5,787,890 | 8/1998 | Reiter et al. ............ 351/215 |

FOREIGN PATENT DOCUMENTS

| | | |
|---|---|---|
| 63-288133 | 11/1988 | Japan . |
| 7155299 | 6/1995 | Japan . |
| WO9203084 | 3/1992 | WIPO . |

*Primary Examiner*—George Manuel
*Attorney, Agent, or Firm*—Fitzpatrick, Cella, Harper & Scinto

[57] ABSTRACT

A eye fundus examining apparatus includes a first optical system for projecting measurement light onto the fundus of an eye, a deflecting member provided in the first optical system for deflecting the measurement light, a light receiving element for receiving the reflected light of the measurement light from the fundus of the eye, a predetermined parameter of a target on the fundus of the eye being measured from the light reception information of the light receiving element, a second optical system for projecting a tracking light beam to an area including the target on the fundus of the eye, an image pickup element for receiving the image of the target illuminated by the tracking light beam, and a control system for driving the deflecting member and directing the measurement light onto the target so that the distance of deviation from the illuminated point by the measurement light under an ideal condition on the fundus of the eye to the target image received on the image pickup element may become a set value, the set value being suitably resettable.

8 Claims, 9 Drawing Sheets

EYE FUNDUS EXAMINING APPARATUS

BACKGROUND OF THE INVENTION

1. Field of the Invention

This invention relates to an eye fundus examining apparatus, for example, used to measure the shape of a blood vessel and a blood stream in the fundus portion of an eye.

2. Related Background Art (1) An eye fundus blood stream meter is an apparatus that irradiates a blood vessel to be measured in the fundus of an eye to be examined with a laser beam, receives the scattered, reflected light thereof with a photodetector, detects the interference signal of a Doppler-shifted component, which is scattered reflected light from the blood vessel and scattered reflected light from a stationary blood vessel wall, frequency-analyzes this data and finds the velocity of the blood stream, the velocity of the blood stream (maximum velocity Vmax) being found from the following equation:

$$Vmax = \{\lambda/(n \cdot \alpha)\} \cdot ||\Delta fmax1| - |\Delta max2||/\cos\beta \quad (1)$$

where Afmax1 and Afmax2 are the maximum shifts of frequencies calculated from received light signals received by two light receiving devices, $\lambda$ is the wavelength of the laser, n is the refractive index of the measured region, $\alpha$ is the angle formed by two light receiving optical axes in the eye, and $\beta$ is the angle formed by a plane formed by the two light receiving optical axes in the eye and the velocity vector of the blood stream.

By effecting the measurement from two directions, the contribution in the direction of incidence of measurement light is offset, and the blood stream in any region on the fundus of the eye can be measured. Also, by making coincident the angle $\beta$ formed by the line of intersection between the plane formed by the two light receiving optical axes and the fundus of the eye and the velocity vector of the blood stream, $\beta=0°$ is established and the true maximum blood stream velocity can be measured.

In this eye fundus blood stream meter utilizing a laser beam to measure the shape of the blood vessel and the velocity of the blood stream in a particular region of the blood vessel in the fundus portion of the eye, it is necessary for the measurement light beam to be accurately applied to the region to be measured within the measuring process time, but actually there is the fine movement or the like of the fixation of the eye to be examined and therefore, it is difficult to continue to apply the measurement light beam accurately to the region to be measured. Accordingly, apparatuses having tracking means for moving the applied position of the measurement light beam on the region to be measured at in real time corresponding to the fine movement of the fixation are disclosed in Japanese Patent Application Laid-Open No. 6-503733 and Japanese Patent Application Laid-Open No. 7-155299.

These apparatuses adopt a system in which tracking light from an illuminating light source in a tracking optical system and measurement light are applied to the fundus of an eye via a pupil-conjugate mirror lying at a position conjugate with the pupil, and the design of the apparatus is such that the spot of the measurement light is applied to a conjugate point on the fundus of the eye at a tracking reference position on a tracking sensor. A blood vessel is illuminated by the tracking light and is enlarged and projected onto a tracking sensor, and the pupil-conjugate mirror is moved so that the image of this blood vessel comes to the tracking reference position, whereby the measurement light always continues to irradiate a predetermined blood vessel.

(2) Also, when effecting measurement by the eye fundus blood stream meter, if the relative position of the optical system of the apparatus and a portion to be measured is changed by the fine movement or the like of the fixation of the eye to be examined, accurate measurement will become difficult and therefore, an apparatus which applies a light beam from a light source for tracking to a blood vessel to be measured, picks up the image of the blood vessel by a CCD camera, and scans the light beam from the light source for tracking so that the image of the blood vessel may be stabilized at a fixed position on the CCD camera, to thereby effect tracking, is disclosed in Japanese Patent Application Laid-Open No. 63-288133. In this apparatus, the reflected scattered light from the portion to be examined is very slight and therefore, light luminance is required of the light source for tracking and green light is suitable from the spectral absorbing characteristic of the fundus of the eye and a blood corpuscle and thus, an He-Ne laser source is used as the light source for tracking.

(a) In the above-described example (1) of the conventional art, however, there will be no problem if the point conjugate with the tracking reference position on the pupil-conjugate mirror and the measurement light spot are coincident with each other, but if the point conjugate with the tracking reference position on the pupil-conjugate mirror and the measurement light spot do not coincide with each other in terms of the structure of the apparatus and the principle of measurement, for example, for the reason when measurement beams are applied at a plurality of different angles, the positions of incidence of the tracking light and the measurement light differ from each other at the cornea position of the eye to be examined and thus, the center of the tracking light on the blood vessel and the measurement light do not coincide with each other. Also, when there is great corneal astigmatism or the like, a deviation occurs between the center of the tracking light on the blood vessel and the measurement light, and there arises the problem that accurate measurement cannot be accomplished in spite of the operating of the tracking system.

(b) Also, in the above-described example (2) of the conventional art, the quantity of scattered reflected light of the light beam from the light source for tracking near the blood vessel to be measured differs greatly depending on the state of the fundus of the eye to be examined or the region to be measured, and the quantity of light necessary to obtain the best image of the blood vessel also becomes different, for example, depending on the thickness of the blood vessel of the eye to be examined. In such a case, the contrast of the image of the blood vessel becomes low and tracking accuracy is reduced and the accuracy of the measurement of the blood stream velocity is also reduced.

SUMMARY OF THE INVENTION

It is a first object of the present invention to solve the above-noted problem (a) and to provide an eye fundus examining apparatus for effecting accurate tracking for a blood vessel to be measured even when measurement light are applied at a plurality of different angles to effect measurement.

It is a second object of the present invention to solve the above noted problem (b) and to provide an eye fundus examining apparatus for accurately effecting tracking to find the velocity of a blood stream exactly in spite of the state of the fundus of an eye to be examined and a region to be measured or the thickness of a blood vessel to be measured.

DESCRIPTION OF THE PREFERRED EMBODIMENTS

Figure 1:
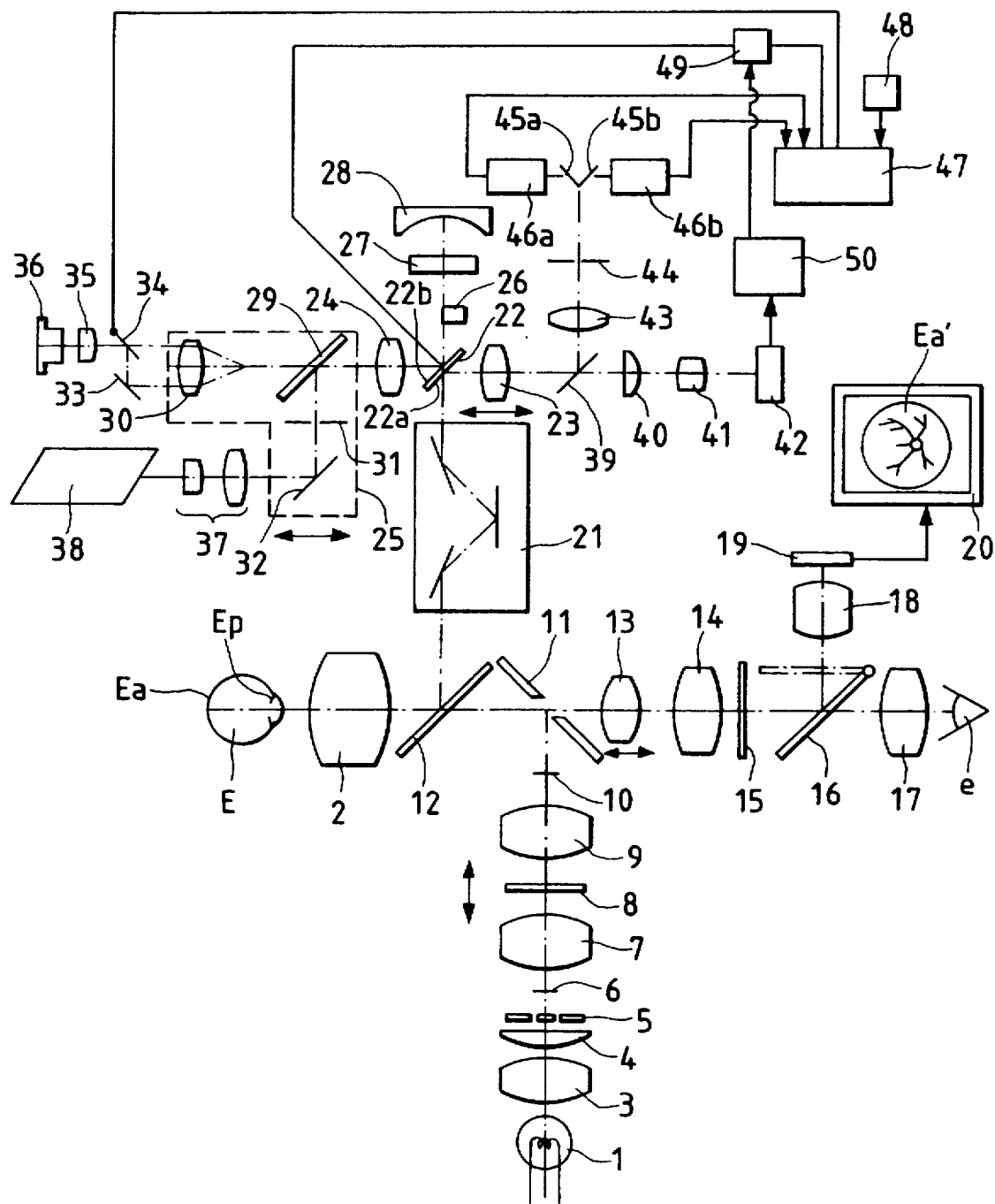
FIG. 1 shows the construction of a first embodiment of the present invention.

The present invention will hereinafter be described in detail with respect to some embodiments thereof shown in the drawings.

FIG. 1 shows the construction of a first embodiment applied to an eye fundus blood stream meter, and on an illuminating optical path leading from a light source 1 for observation, comprising a tungsten lamp or the like emitting white light, to an objective lens 2 opposed to an eye E to be examined, there are successively arranged a condenser lens 3, a field lens 4 with a band-pass filter transmitting therethrough, for example, only light of a wavelength in the yellow range, a ring slit 5 substantially conjugate with the pupil Ep of the eye E to be examined, a light intercepting member 6 substantially conjugate with the crystalline lens of the eye E to be examined, a relay lens 7, a transmission type liquid crystal plate 8 which is a fixation target displaying element movable along the optical path, a relay lens 9, a light intercepting member 10 conjugate with the vicinity of the cornea of the eye E to be examined, an apertured mirror 11 and a band-pass mirror 12 transmitting therethrough light of a wavelength in the yellow range and almost reflecting the other light beams, whereby there is constructed an illuminating optical system.

An eye fundus observation optical system is constructed behind the apertured mirror 11, and there are successively arranged a focusing lens 13 movable along the optical path, a relay lens 14, a scale plate 15, an optical path changeover mirror 16 removably insertable into the optical path, and an eyepiece 17, and this optical system leads to an examiner's eye e. A TV relay lens 18 and a CCD camera 19 are disposed on the optical path in the direction of reflection when the optical path changeover mirror 16 is inserted in the optical path, and the output of the CCD camera 19 is connected to a liquid crystal monitor 20.

An image rotator 21 and a galvanometric mirror 22, having a rotary shaft perpendicular to the plane of the drawing sheet of FIG. 1 and having its both surfaces polished, are disposed on the optical path in the direction of reflection of the band-pass mirror 12, a focusing lens 23 movable along the optical path is disposed in the direction of reflection of the lower reflecting surface 22a of the galvanometric mirror 22, and a lens 24 and a focusing unit 25 movable along the optical path are disposed in the direction of reflection of the upper reflecting surface 22b of the galvanometric mirror 22. The front side focal plane of the lens 24 is in conjugate relationship with the pupil Ep of the eye E to be examined, and the galvanometric mirror 22 is disposed on that focal plane.

Also, above the galvanometric mirror 22, there are concentrically arranged an optical path length correcting semicircular plate 26, a black spot plate 27 having a light intercepting portion in the optical path, and a concave mirror 28 on the optical path, and these cooperate with one another to constitute a relay optical system for directing a light beam passing through the galvanometric mirror 22 without being reflected by the lower reflecting surface 22a thereof so as to return to the upper reflecting surface 22b of the galvanometric mirror 22. The optical path length correcting semicircular plate 26 is for correcting the vertical deviation of the positions of the upper reflecting surface 22b and lower reflecting surface 22a of the galvanometric mirror 22 caused by the thickness of the mirror, and acts only in the optical path leading toward the image rotator 21.

In the focusing unit 25, a dichroic mirror 29 and a condensing lens 30 are successively arranged on the same optical path as that of the lens 24, and on the optical path in the direction of reflection of the dichroic mirror 29, there are disposed a mask 31 and a mirror 32, and this focusing unit 25 is integrally movable in the direction of the arrow.

On the optical path in the direction of incidence of the condensing lens 30, there are disposed in parallel, a fixed mirror 33 and an optical path changeover mirror 34 retractable from the optical path, and on the optical path in the direction of incidence of the optical path changeover mirror 34, there are successively arranged a collimator lens 35 and a light source 36 for measurement, such as a laser diode emitting coherent infrared light. Further, on the optical path in the direction of incidence of the mirror 32, there are arranged a beam expander 37 comprising a cylindrical lens or the like, and a light source 38 for tracking, such as an He-Ne laser source emitting, for example, green light of high luminance differing from the other light source.

On the optical path in the direction of reflection of the lower reflecting surface 22a of the galvanometric mirror 22, there are successively arranged a focusing lens 23, a dichroic mirror 39, a field lens 40, a magnifying lens 41 and a one-dimensional CCD 42 with an image intensifier, whereby there is constituted a blood vessel detecting optical system. Also, on the optical path in the direction of reflection of the dichroic mirror 39, there are disposed an imaging lens 43, a confocal stop 44 and a pair of mirrors 45a and 45b provided substantially conjugately with the pupil Ep of the eye E to be examined, and in the directions of reflection of the pair of mirrors 45a and 45b, there are disposed photomultipliers 46a and 46b, respectively, whereby a light receiving optical system for measurement is constituted. While all optical paths are shown on the same plane for convenience of display of the device in FIG. 1, the reflecting optical paths of the pair of mirrors 45a and 45b, the measuring optical path in the direction of emergence of the light source 38 for tracking and the optical path leading from the light source 36 to measurement to the mask 31 are orthogonal to the plane of the drawing sheet of FIG. 1.

There is further provided a system controlling portion 47 for controlling the entire apparatus, and input means 48 to be operated by the examiner and the outputs of the photomultipliers 46a and 46b are connected to the system controlling portion 47, the output of which is connected to the galvanometric mirror 22 through a galvanometric mirror control circuit 49 and is also connected to the optical path changeover mirror 34. The output of the one-dimensional CCD 42 is connected to the galvanometric mirror control circuit 49 through a blood vessel position detecting circuit 50.

Figure 2:
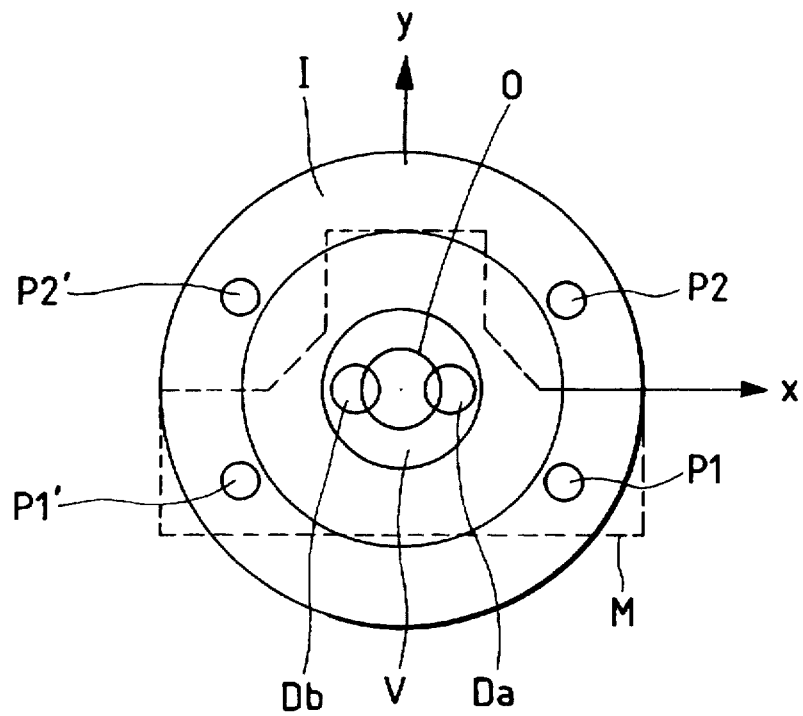
FIG. 2 is an illustration of the disposition of light beams on a pupil.

FIG. 2 shows the disposition of light beams on the pupil Ep of the eye E to be examined, I indicates the image of the ring slit 5 in an area illuminated by yellow illuminating light, O designates an eye fundus observation light beam or the image of the opening portion of the apertured mirror 11, V denotes a measurement/blood vessel light receiving light beam or the images of the effective portions of the upper and lower reflecting surfaces 22a and 22b of the galvanometric mirror 22, and Da and Db designate two measurement light receiving light beams or the images of the pair of mirrors 45a and 45b. Also, P2 and P2' indicate the positions of measurement light selected by changing over the optical path changeover mirror 34 at the position of incidence of the measurement light, and an area M indicated by the dot-and-dash line is the image of the lower reflecting surface 22a of the galvanometric mirror 22.

White light emitted from the light source 1 for observation passes through the condenser lens 3, and only light of yellow wavelength is transmitted through the field lens 4, and passes through the ring slit 5, the light intercepting member 6 and the relay lens 7, and illuminates the transmission type liquid crystal 8 behind it. Further, this light beam passes through the relay lens 9 and the light intercepting member 10 and is reflected by the apertured mirror 11, and only light of a wavelength in the yellow range is transmitted through the band-pass mirror 12 and passes through the objective lens 2, and is once formed as an eye fundus illuminating light beam image I on the pupil Ep of the eye E to be examined, whereafter it substantially uniformly illuminates the fundus Ea of the eye. At this time, a fixation target is displayed on the transmission type liquid crystal plate 8, and is projected onto the fundus Ea of the eye E to be examined by the illuminating light, and is presented as a fixation target image to the eye E to be examined. The ring slit 5 and the light intercepting members 6 and 10 are for separating eye fundus illuminating light and eye fundus observation light from each other at the front eye part of the eye E to be examined, and may be of any shape if they form the necessary light intercepting areas.

Reflected light from the fundus Ea of the eye is taken out as an eye fundus observation light beam O from on the pupil Ep and returns along the same optical path, and passes through the central opening portion of the apertured mirror 11, the focusing lens 13 and the relay lens 14, and is formed as an eye fundus image Ea' on the scale plate 15, whereafter it comes to the optical path changeover mirror 16. When the optical path changeover mirror 16 is retracted from the optical path, the eye fundus image Ea' becomes observable by the examiner's eye e through the eyepiece 17, and on the other hand, when the optical path changeover mirror 16 is inserted in the optical path, the eye fundus image Ea' formed on the scale plate 15 is re-imaged on the CCD camera 19 by the TV relay lens 18 and is displayed on the liquid crystal monitor 20.

The examiner effects the alignment of the apparatus by the eyepiece 17 or the liquid crystal monitor 20 while observing the eye fundus image Ea'. At this time, it is preferred to adopt an appropriate observation system in conformity with that purpose, and the case of the observation by the eyepiece 17 is generally higher in resolution and sensitivity than the liquid crystal monitor 20, etc. and therefore is suitable for reading any minute change in the fundus Ea of the eye and diagnosing. On the other hand, in the case of the observation by the liquid crystal monitor 20, the field of view is not limited and therefore, the examiner's fatigue can be mitigated and further, by connecting the output of the CCD camera 19 to an outside video tape recorder, a video printer or the like, changes in the measured region on the fundus Ea of the eye can be successively electronically recorded, and this is clinically very effective.

Next, measurement light emitted from the light source 36 for measurement is collimated by the collimator lens 35, and is reflected by the optical path changeover mirror 34 and the fixed mirror 33 when the optical path changeover mirror 34 is inserted in the optical path, and passes below the condensing lens 30, and passes directly above the condensing lens 30 when the optical path changeover mirror 34 is retracted from the optical path, and is transmitted through the dichroic mirror 29.

On the other hand, tracking light emitted from the light source 38 for tracking has its beam diameter enlarged at different vertical and horizontal magnifications by the beam expander 37, and is reflected by the mirror 32, whereafter it is shaped into a desired shape by the shaping mask 31, and is reflected by the dichroic mirror 29 and is superposed on the measurement light imaged in the shape of a spot at a position conjugate with the center of the opening portion of the mask 31, by the condensing lens 30.

The tracking light superposed on the measurement light passes through the lens 24, is once reflected by the upper reflecting surface 22b of the galvanometric mirror 22, and passes through the black spot plate 27, whereafter it is reflected by the concave mirror 28 and again passes through the black spot plate 27 and the optical path length correcting semicircular plate 26, and is returned toward the galvanometric mirror 22. The galvanometric mirror 22 is disposed at a position conjugate with the pupil Ep of the eye E to be examined and therefore, the image thereof is of a shape shown by broken line M in FIG. 2 on the pupil Ep of the eye E to be examined.

The concave mirror 28, the black spot plate 27 and the optical path length correcting semicircular plate 26 are concentrically disposed on the optical path, and are given the function of a relay optical system for imaging the upper reflecting surface 22b and lower reflecting surface 22a of the galvanometric mirror 22 by −1 time and thus, light beams reflected at positions P1 and P1' in FIG. 2 on the back of the image M of the galvanometric mirror 22 by the insertion and retraction of the optical path changeover mirror 34 into and from the optical path are returned to positions P2 and P2' lying in the cut-away portion of the galvanometric mirror 22, and are not reflected by the galvanometric mirror 22, but travel toward the image rotator 21. The light beams deflected toward the objective lens 2 by the band-pass mirror 12 via the image rotator 21 are applied to the fundus Ea of the eye E to be examined through the objective lens 2.

As described above, the measurement light and the tracking light are reflected in the upper reflecting surface 22b of the galvanometric mirror 22, and when they are again returned, they enter the galvanometric mirror 22 while being eccentric from the optical axis of the objective lens 2 and therefore, they are formed as a spot image P2 or P2' on the pupil Ep as shown in FIG. 2, whereafter they irradiate the fundus Ea of the eye into the shape of a spot.

The scattered reflected light on the fundus Ea of the eye is again condensed by the objective lens 2, is reflected by the band-pass mirror 12, passes through the image rotator 21, is reflected by the lower reflecting surface 22a of the galvanometric mirror 22, passes through the focusing lens 23, and on the dichroic mirror 39, the measurement light and the tracking light are separated from each other.

The tracking light is transmitted through the dichroic mirror 39 and formed as a blood vessel image Ev' more enlarged than the eye fundus image Ea' by the eye fundus observation optical system on the one-dimensional CCD 42 by the field lens 40 and the imaging lens 41. On the basis of the blood vessel image Ev' picked up by the one-dimensional CCD 42, data representative of the amount of movement of the blood vessel image Ev' is prepared in the blood vessel position detecting circuit 50 and is outputted to the galvanometric mirror control circuit 49. The galvanometric mirror control circuit 49 drives the galvanometric mirror 22 so as to compensate for this amount of movement.

On the other hand, the measurement light is reflected by the dichroic mirror 39, passes through the lens 43 and the opening portion of the confocal stop 44, is reflected by the pair of mirrors 45a and 45b and is received by the photomultipliers 46a and 46b. The outputs of the photomultipliers 46a and 46b are outputted to the system controlling portion 47, and this light reception signal is frequency-analyzed as in the conventional art, whereby the blood stream velocity of the fundus Ea of the eye is found.

At this time, due to the spectral characteristic of the band-pass mirror 12, the illuminating light from the light source 1 for observation does not arrive at the one-dimensional CCD 42, and further, the image pickup range is set narrowly and therefore, it is difficult for harmful flare light to mix with the illuminating light and thus, only the blood vessel image Ev' by the tracking light is picked up by the one-dimensional CCD 42. Also, hemoglobin in blood and melanin on the epithelium of pigment greatly differ in the spectral reflectance in the green wavelength range from each other and therefore, by making the tracking light into green light, it becomes possible to pick up the blood vessel image Ev' with good contrast.

The light beam received by the one-dimensional CCD 42 is a light beam taken out of a measurement/blood vessel light receiving light beam V on the pupil Ep of the eye E to be examined, and from this light beam V, light beams passing through measurement light receiving light beams Da and Db are taken out by the pair of mirrors 45a and 45b and are received by the photomultipliers 46a and 46b. It is because the one-dimensional CCD 42 is greater in the imaging magnification on the fundus of the eye than the CCD camera 19 of the eye fundus observation optical system and the illuminance of the image plane on the one-dimensional CCD 42 is difficult to secure, that the measurement/blood vessel light receiving light beam V is made large as compared with the eye fundus observation light beam O.

On the other hand, the influence of flare light created on the front eye part of the eye E to be examined by making the light beam large poses no problem because the blood vessel image receiving optical system is smaller in the image receiving range. Also, the spacing on the pupil Ep between the measurement light receiving light beams Da and Db directly affects the resolving power of the blood stream velocity meter, but by making the measurement/blood vessel light receiving light beam V large, it becomes possible to sufficiently secure the spacing between the measurement light receiving light beams Da and Db.

Also, a part of the scattered reflected light on the fundus Ea of the eye by the measurement light and the tracking light is transmitted through the band-pass mirror 12 and directed to the eye fundus observation optical system behind the apertured mirror 11. At this time, the tracking light is imaged as a bar-like indicator T on the scale plate 15, and the design of the apparatus is such that the conjugate point on the fundus of the eye with the tracking reference position initially set on the tracking sensor becomes the center of the indicator T and therefore, the measurement light is formed as a spot image on the central portion of this indicator T.

Figure 3:
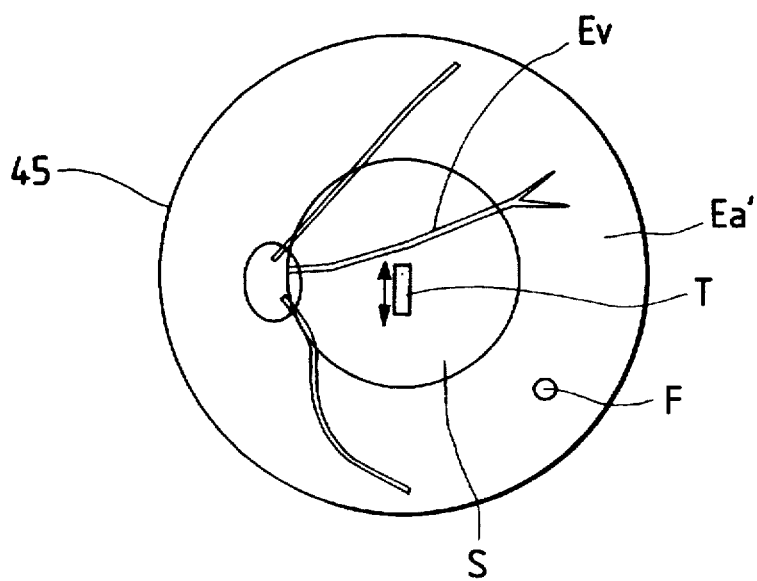
FIG. 3 is an illustration of an examiner's field of view.

As shown in FIG. 3, these images are observed with the eye fundus image Ea' and the fixation target image F through the eyepiece 17 or the liquid crystal monitor 20. At this time, a spot image, not shown, is observed as being superposed on the center of the indicator T, and the indicator T can be one-dimensionally moved within the range of a truly circular scale S at the center of the field of view prepared in advance on the scale plate 15 projected onto the fundus Ea of the eye, by an operating member such as the operating rod of the input means 48.

The examiner first effects the focusing of the eye fundus image Ea'. When the focusing knob of the input means 48 is adjusted, the transmission type liquid crystal plate 8, the focusing lenses 13 and 23 and the focusing unit 25 are moved along the optical path in operative association with one another by driving means, not shown. When the eye fundus image Ea' is just focused, the transmission type liquid crystal plate 8, the scale plate 15, the one-dimensional CCD 42 and the confocal stop 44 simultaneously become conjugate with the fundus Ea of the eye.

Figure 4:
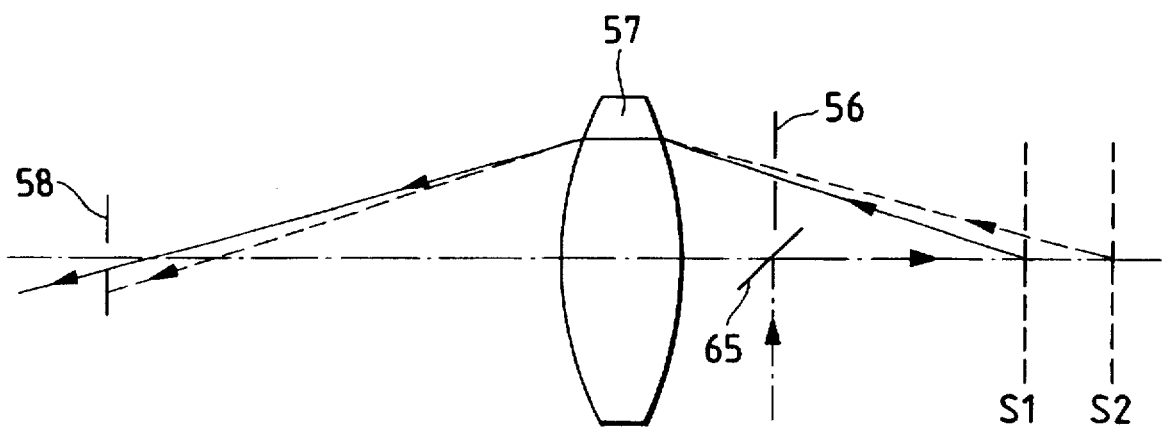
FIG. 4 is an illustration of a confocal stop.
Figure 5:
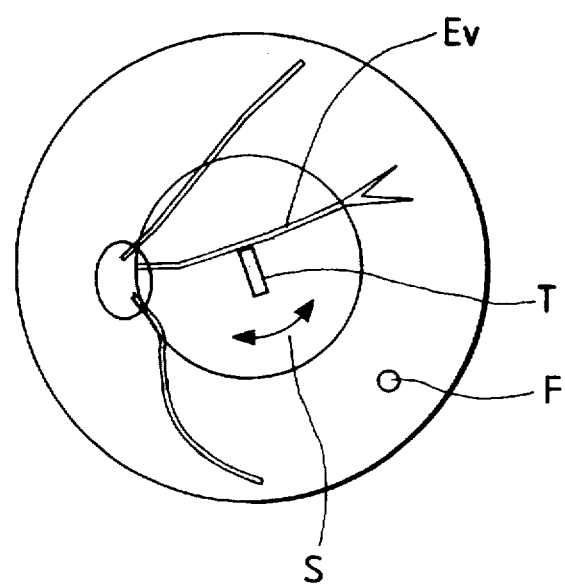
FIG. 5 is an illustration of the examiner's field of view.
Figure 6:
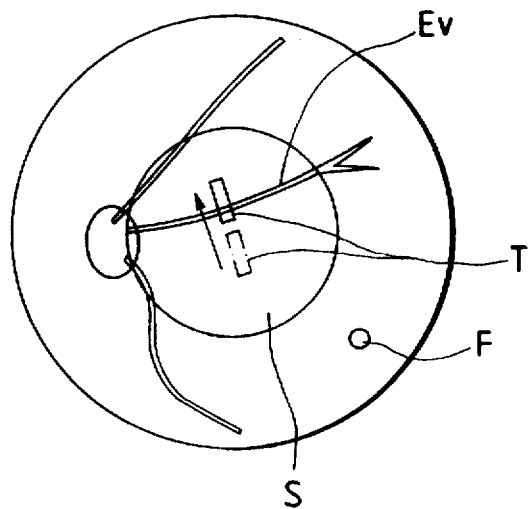
FIG. 6 is an illustration of the examiner's field of view.

The confocal stop 44 at this time is for focusing on a desired blood vessel Ev, and FIG. 4 is an illustration of the action thereof, and the position of the blood vessel Ev on the fundus Ea of the eye, which is the object of measurement, is represented by a measured region S1, and the position of the blood vessel Ev in choroidea Sc lying rearwardly of this blood vessel Ev is represented by a measured region S2.

The light beam from the light source 36 for measurement enters the mirror 65 from below it, is reflected in a horizontal direction and irradiates the measured region S1. The reflected light on the measured region S1 passes through an opening 56 having the function of determining the light receiving direction which is equal to that of the pair of mirrors 45a and 45b, and is made conjugate with the measured region S1 by a lens 57 and passes through a small aperture 58, and thereafter is received by the photomultipliers 46a and 46b, not shown. In this optical system, the reflected light on the measured region S2 indicated by a dotted line, like the light beam reflected by the measure region S1 indicated by solid line, is imaged by the lens 57, but cannot pass through the small aperture 58 and therefore, this light beam is not received by the photomultipliers 46a and 46b.

As described above, in the present embodiment, provision is made of for the confocal stop 44 to have a function similar to that of the above-mentioned small aperture 58, and only the reflected light on the blood vessel Ev at a particular depth is received by the photomultipliers 46a and 46b, whereby it becomes possible to measure the blood stream velocity of a desired blood vessel Ev. In the actual examination, the examiner sets the depth of the blood vessel Ev which is the object of measurement while watching the focus state on the eye fundus image Ea' shown in FIG. 3, and focuses the eye fundus image Ea'.

Figure 15:
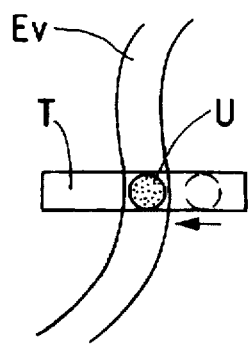
FIG. 15 is an illustration of the positional correction of measurement light.

After the focusing has been terminated, the examiner operates the input means 48 to move the fixation target image F, and directs the visual axis of the eye E to be examined and changes the observation area, and moves the blood vessel Ev, which is the object of measurement, into the circle S of the scale plate 15. Then, as shown in FIG. 15, the examiner operates the image rotator 21 by the operating rod of the input means 48 to rotate the indicator T so that the indicator T may become perpendicular to the direction of running of the blood vessel Ev, which is the object of measurement.

At this time, the eye fundus observation light does not pass through the image rotator 21 and therefore, only the indicator T is recognized as being rotated and accordingly, the image of each optical member on the pupil Ep shown in FIG. 2 is also rotated by the same angle in the same direction about the origin, and a straight line passing through the centers of the measurement light receiving light beams Da and Db and a straight line passing through the centers of the spot images P1 (P2) and P1' (P2'), i.e., the x-axis, coincides with the direction of running of the blood vessel Ev.

This operation corresponds to the fact that β=0° in equation (1) for the calculation of velocity described in the example of the conventional art, whereby the following advantages (a)-(c) arise.

(a) When from equation (1), β=90°, that is, cosβ=0, the absolute value of the maximum blood stream velocity Vmax cannot be found from only the maximum frequency shifts Δfmax1 and Δfmax2, but the eye fundus image Ea' is rotated so that β=0°, whereby a measurement impossible position can be avoided.

(b) It becomes unnecessary to measure the angle β and therefore, error factors decrease and the operation is simplified.

(c) As described in the example of the conventional art, the blood stream velocity is found from the interference signal of the scattered reflected light from the blood vessel wall and the scattered reflected light in the blood and therefore, even if the fundus Ea of the eye moves in the direction of the x-axis during measurement, the result of measurement will not be affected if the blood vessel Ev is made substantially parallel to the direction of the x-axis.

On the other hand, when the fundus Ea of the eye moves in the direction of the y-axis orthogonal to the x-axis, the light beam from the light source 36 for measurement deviates from the blood vessel Ev in the measured region and the measured value becomes unstable, but in that case, the amount of movement of the blood vessel Ev can be detected with respect only to the direction of the y-axis, and in the present embodiment; tracking in only this one direction is effected by the blood vessel detecting optical system behind the dichroic mirror 39 and the galvanometric mirror 22.

To effect this tracking and measure the blood stream velocity accurately and quickly with respect to all blood vessels Ev to be examined, the one-dimensional CCD 42 for detecting the amount of movement of the blood vessel image Ev' may preferably be disposed perpendicularly to the blood vessel Ev, which is the object of measurement, and further, by rendering β=0°, the advantage that it becomes unnecessary to use a two-dimensional sensor also arises.

Figure 7:
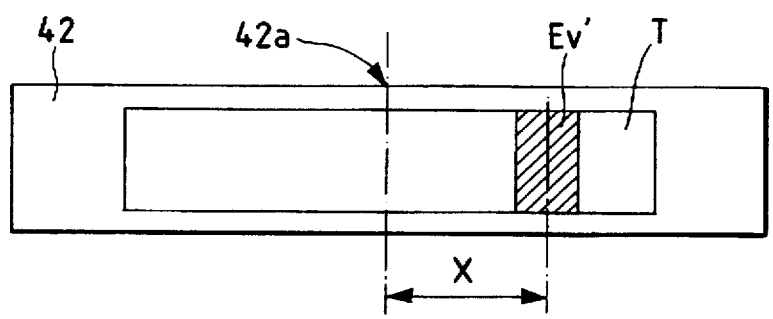
FIG. 7 is an illustration of the position of the image of a blood vessel on a one-dimensional CCD.

The operating rod of the input means 48 is operated to adjust the angles of the indicator T (tracking light) and the measured blood vessel Ev so as to be orthogonal to each other, and move the blood vessel Ev in the lengthwise direction of the indicator T. When a portion of the indicator T becomes orthogonal to and overlaps the measured blood vessel Ev, the blood vessel image Ev' indicated and illuminated by the tracking light (indicator T) as shown in FIG. 7 is enlarged and picked up on the element of the one-dimensional CCD 42 of the blood vessel detecting optical system arranged in the lengthwise direction of the tracking light.

The reflected light of the tracking light (indicator T) projected onto the fundus Ea of the eye is projected onto the one-dimensional CCD 42 at −n times via the rotator 21 and the galvanometric mirror 22 and therefore is stationary on the one-dimensional CCD 42 in spite of the apparent movement of the indicator T (tracking light) and when the indicator T (tracking light) moves in the lengthwise direction, only the blood vessel image Ev' moves on the one-dimensional CCD 42.

After the measured region is determined, the input means 48 is again operated to input the start of tracking. When a command for starting the tracking is inputted from the input means 48 to the galvanometric mirror control circuit 49 through the controlling portion 47, the measurement light is applied while being superposed on the tracking light and at the same time, in the blood vessel position detecting circuit 50, the amount of movement X of the blood vessel image Ev' shown in FIG. 7 from the one-dimensional reference position 42a is calculated on the basis of the light reception signal of the one-dimensional CCD 42. On the basis of this amount of movement X, the galvanometric mirror 22 is driven by the galvanometric mirror control circuit 49, and the received position of the blood vessel image Ev' on the one-dimensional CCD 42 is controlled so as to be on the one-dimensional reference position 42a. Since the measurement light in the form of a beam spot is applied while being superposed on the central position corresponding to the one-dimensional reference position 42a of the tracking light (indicator T) on the fundus Ea of the eye, it becomes possible to grasp the measured blood vessel Ev accurately by the tracking system.

Figure 8:
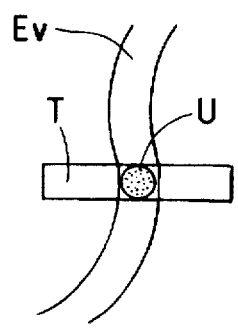
FIG. 8 is an illustration of the positions of tracking light and measurement light.
Figure 9:
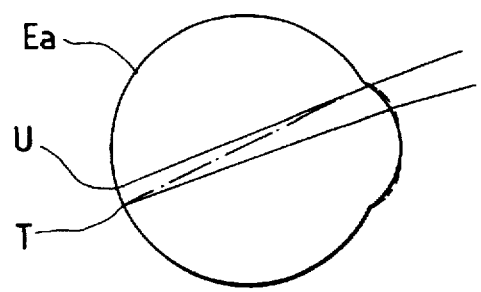
FIG. 9 is an illustration of the positional deviation between the tracking light and the measurement light.
Figure 10:
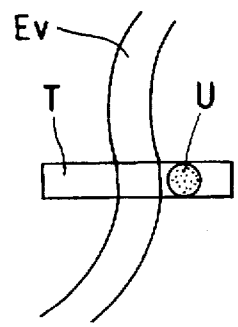
FIG. 10 is an illustration of the positional deviation of the measurement light.

The design of the device is made such that if P1 (P1') and P2 (P2') are points conjugate with the tracking reference position when the measurement light passes, the central position of the tracking light T lies at the tracking reference position on the fundus Ea of the eye as shown in FIG. 8 when the tracking light and the measurement light are the same light beam and enter the eye E to be examined and therefore, the measurement light U is imaged at this position and the tracking system functions effectively. However, when the angles of incidence of the tracking light T and the measurement light U onto the cornea differ from each other and particularly when there is great astigmatism in the cornea or the like, the imaged positions of the tracking light T and the measurement light U on the fundus of the eye deviate from each other as shown in FIG. 9, and the measurement light U deviates from the center of the tracking light T, i.e., the blood vessel Ev, as shown in FIG. 10.

Figure 11:
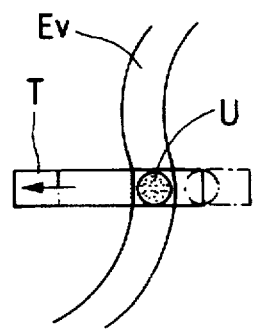
FIG. 11 is an illustration of the positional correction of the tracking light.

Accordingly, as shown in FIG. 11, during tracking, the galvanometric mirror 22 is driven by an amount of correction from the input means 48 through the controlling portion 47, and on the fundus Ea of the eye, the measurement light U is moved to the position of the blood vessel Ev with the tracking light T.

Figure 12:
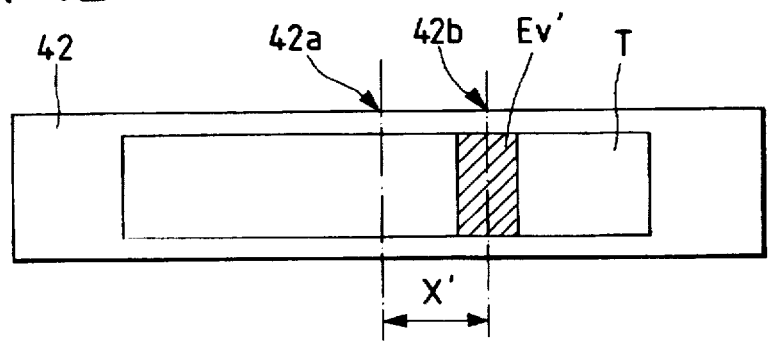
FIG. 12 is an illustration of the position of the image of a blood vessel on a one-dimensional CCD.

Seeing this on the one-dimensional CCD 42, it follows that as shown in FIG. 12, the blood vessel image Ev' is projected while deviating by X' from an initially set one-dimensional reference position 42a. With this position 62b spaced apart by X' as a new one-dimensional reference position, the correcting operation is performed by tracking control, whereby the measurement light U can grasp the measured blood vessel Ev accurately. That is, this means that a set value, to which the distance of deviation from the initially set one-dimensional reference position, which is the irradiated position under ideal conditions, to the blood vessel image position is to be adjusted by the tracking operation, has been changed from zero to X'.

Figure 13:
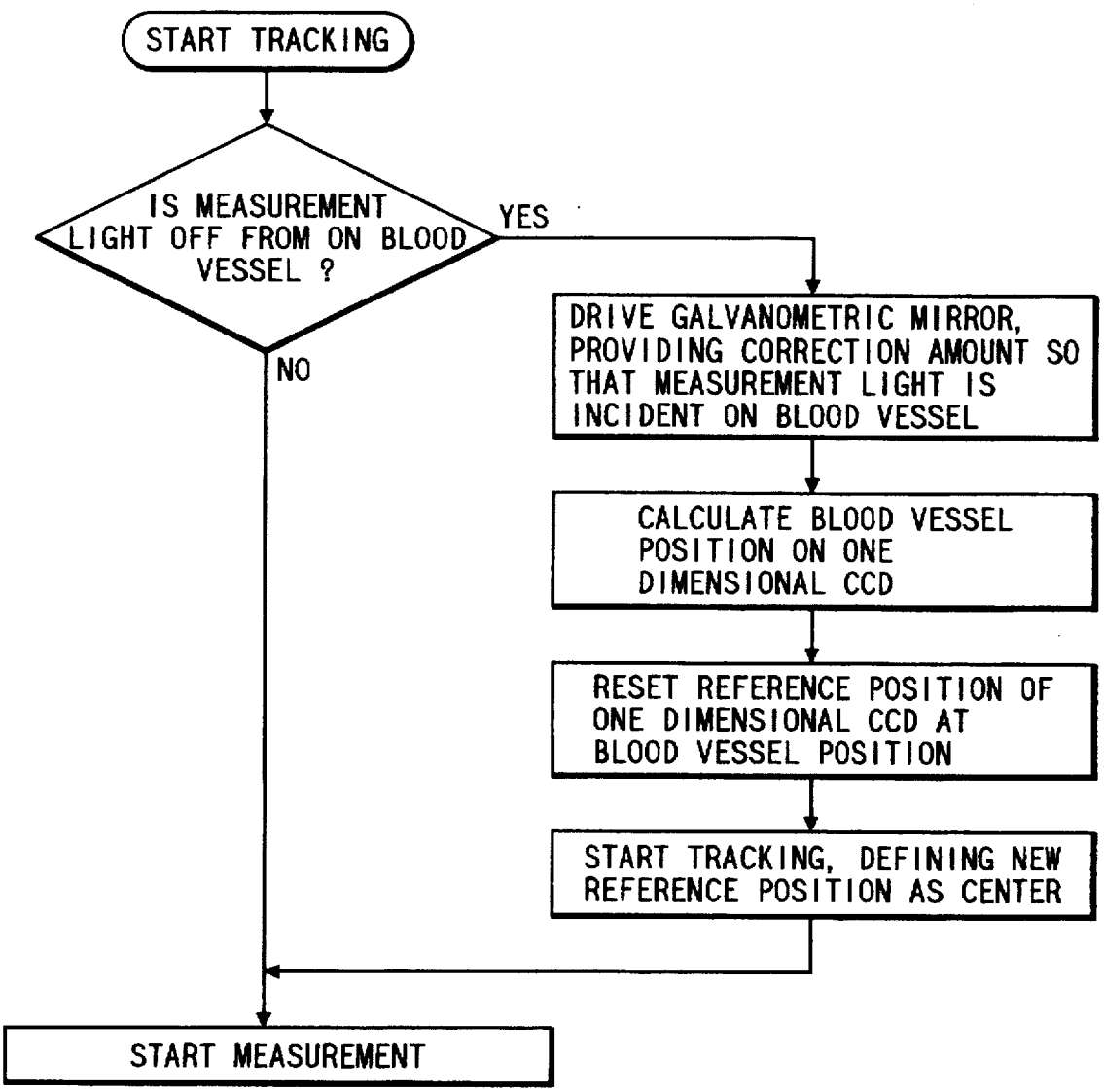
FIG. 13 is a flow chart of tracking correction.

FIG. 13 is a flow chart of tracking correction. When tracking is started, whether the measurement light U deviates from the measured blood vessel Ev is first detected, and if it does not deviate, measurement is started. If it deviates, an amount of correction is provided so that the measurement light U may come onto the blood vessel Ev, and the galvanometric mirror 22 is driven. Next, the position of the blood vessel Ev is detected on the one-dimensional CCD 42, and at that position of the blood vessel Ev, the resetting of the reference position is effected. Tracking is then started with the new reference position as the center, whereafter measurement is started.

Figure 14:
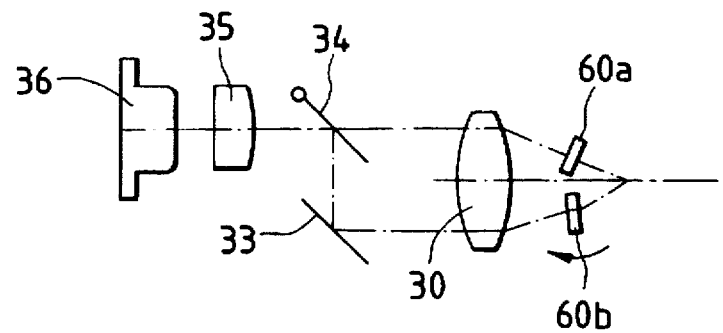
FIG. 14 shows the construction of a first modification of a measurement-light-applying optical system.

Referring now to FIG. 14 which shows a first modification of the first embodiment, plane parallel plates 60a and 60b are provided in the measurement optical path between the dichroic mirror 29 and the condensing lens 30, and each of them is rotatable on a shaft perpendicular to the plane of the drawing sheet of FIG. 14 by a driving mechanism, not shown.

When tracking is started and on a finder or a monitor, the measurement light deviates from the center of the tracking light on the measured blood vessel as shown in FIG. 10, the plane parallel plates 60a and 60b are driven by the input means 48, whereby the optical path of the measurement light U is shifted as shown in FIG. 15, and measurement is effected with the measurement light spot U moved so as to come onto the blood vessel Ev.

Figure 16:
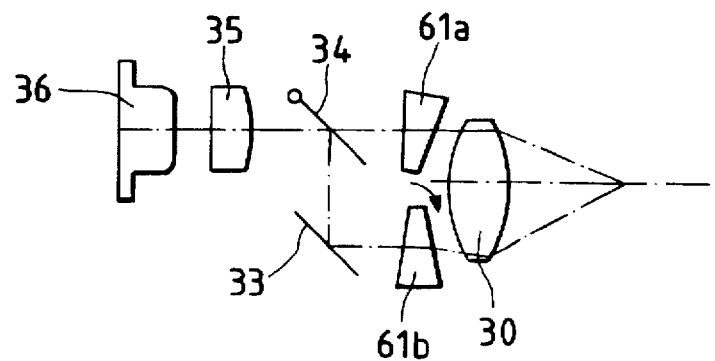
FIG. 16 shows the construction of a second modification of the measurement-light-applying optical system.

Referring to FIG. 16 which shows a second modification, instead of the plane parallel plates 60a and 60b, optical members 60a and 60b of a wedge-like cross-sectional shape are used between the condensing lens 30 and the optical path changeover mirror 34 and between the condensing lens 30 and the fixed mirror 33, respectively.

Further, as a third modification, no optical member is used, but the design of the device is such that the position of the light source 36 for measurement can be freely changed on a plane perpendicular to the plane of the drawing sheet of FIG. 16 and the optical path, whereby a similar operational effect can be obtained.

Figure 17:
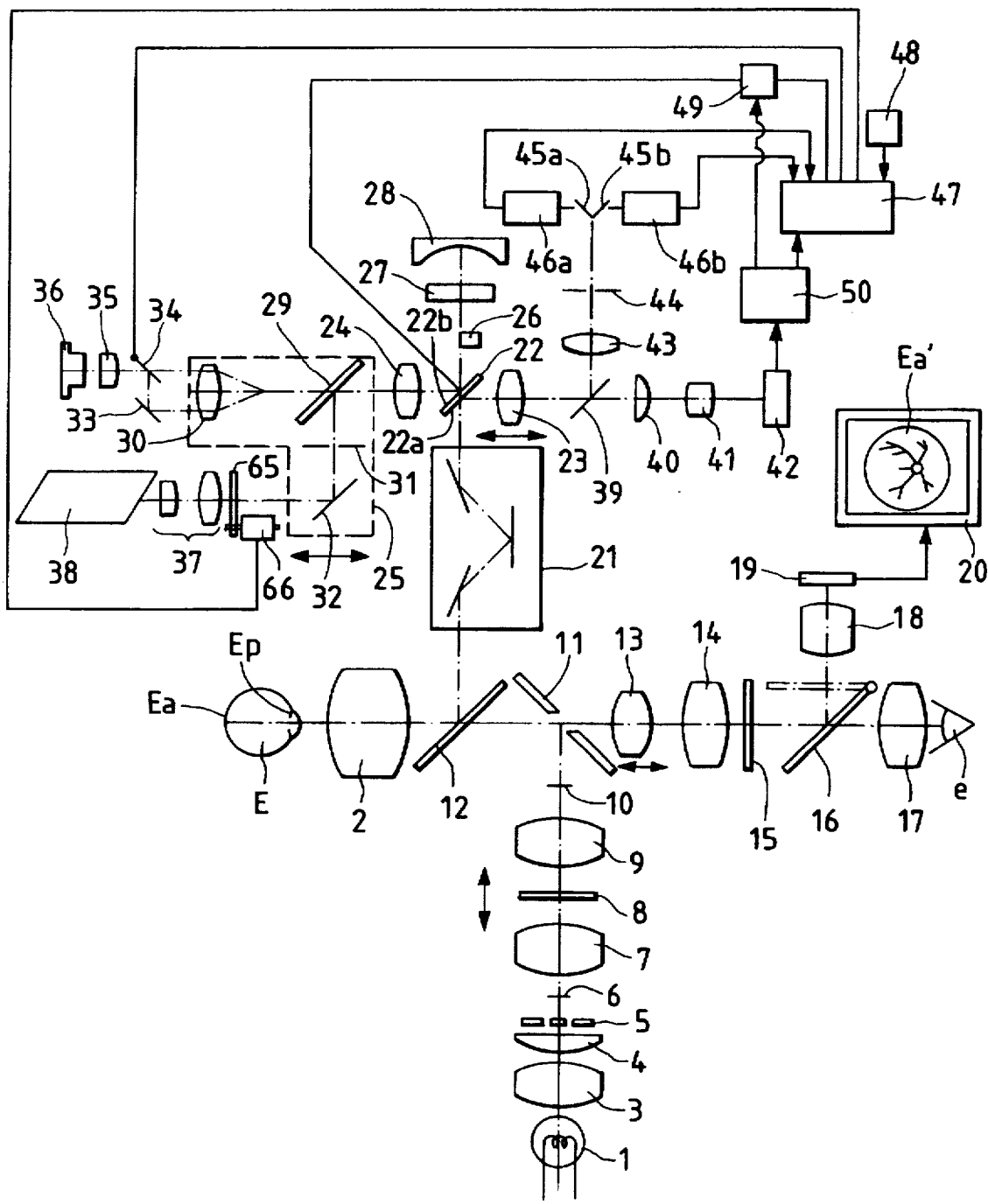
FIG. 17 shows the construction of a second embodiment of the present invention.

Referring to FIG. 17 which shows the construction of a second embodiment, a gradation ND filter 65 partially differing in transmittance is disposed between the mirror 32 and the beam expander 37. Gradation ND filter driving means 66 such as a motor is connected to the gradation ND filter 65 through a gear, and the output of the system controlling portion 47 is connected to the gradation ND filter 65. Thereby, there is formed tracking light power control means in which the gradation ND filter 65 is moved in a plane perpendicular to the optical path. The tracking light power control means may use, instead of the gradation ND filter 65, ND filters differing in transmittance from one another and arranged in the form of a turret. The other portion of the second embodiment is constituted by an optical system and a control system similar to those in the first embodiment of FIG. 1.

Figure 18A:
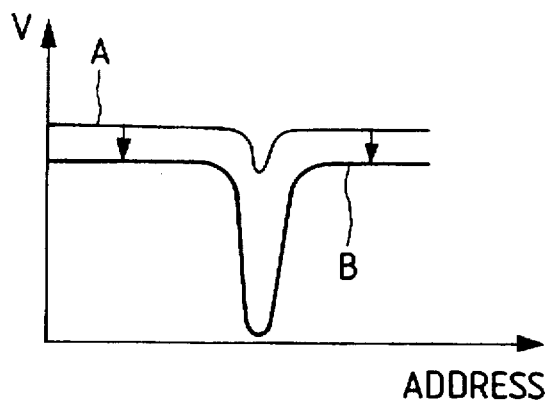
FIGS. 18A and 18B are graphs of the output voltage of the one-dimensional CCD.
Figure 18B:
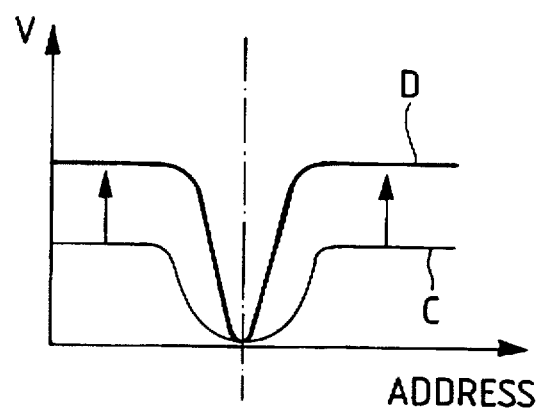
Figure 19:
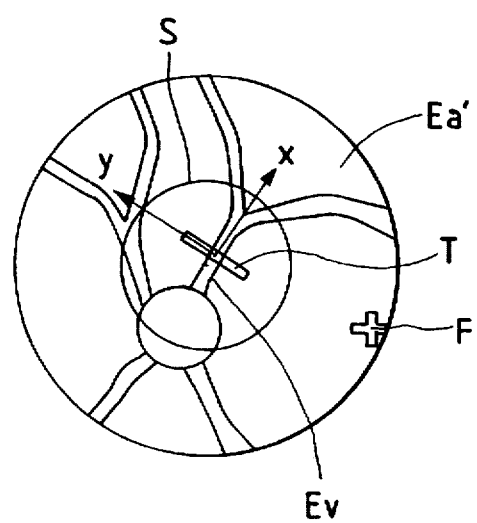
FIG. 19 is an illustration of an examiner's field of view.

FIGS. 18A and 18B show the output voltage of the blood vessel image Ev' picked up by the one-dimensional CCD 42, and the axis of the abscissas represents the address of the one-dimensional CCD 42, and the axis of the ordinates represents the voltage V. If the quantity of applied tracking light is too great, the blood vessel image Ev' of a thin blood vessel will be broken as shown by A in FIG. 18A, and if the quantity of applied tracking light is too small, sufficient resolution will not be obtained as shown by C in FIG. 18B and therefore, the system controlling portion 47 drives the gradation ND filter 65 by the gradation ND filter driving means 66 so that an appropriate blood vessel image Ev' may be obtained from the blood vessel image Ev', and optimizes the tracking light from the light source 38 for tracking into a predetermined quantity of applied light. Thereby, there is obtained a blood vessel image of light contrast as indicated by B and D in FIGS. 18A and 18B.

With regard also to measurement, the operations other than the controlling of the tracking light by the gradation ND filter 65 can be performed entirely similarly to those in the first embodiment and need not be described.

The elements of the one-dimensional CCD 42 are arranged in the lengthwise direction of the tracking light, and when the adjustment of the angle of the measured region has been terminated, the lengthwise direction of the indicator T showing the tracking light is orthogonal to the direction of running of the measured blood vessel Ev and therefore, the eye fundus image Ea' indicated by the indicator T is enlargedly picked up on the one-dimensional CCD 42 of the blood vessel detecting optical system.

After the adjustment of the angle has been terminated, the operating rod of the input means 48 is operated to move the indicator T, and the spot image superposed on the tracking light is made coincident with the measured region to thereby select the measured region, and after the measured region has been determined, the input means 48 is operated again to input the starting of tracking.

When a command for starting tracking is inputted from the input means 48 to the galvanometric mirror control circuit 49 through the system controlling portion 47, if the contrast of the blood vessel image Ev' exceeds a desired value, the amount of movement of the blood vessel image Ev' from the one-dimensional reference position is calculated in the blood vessel position detecting circuit 50 on the basis of the light reception signal of the one-dimensional CCD 42. On the basis of this amount of movement, the galvanometric mirror 22 is driven by the galvanometric mirror control circuit 49, and the received position of the blood vessel image Ev' on the one-dimensional CCD 42 is controlled so as to become constant.

Also, when the contrast of the blood vessel image Ev' does not exceed the desired value, the system control means 47 controls the gradation ND filter driving means 66 in conformity with the blood vessel image Ev', and controls the tracking light so that a blood vessel image Ev' of high contrast may be obtained, whereafter in the blood vessel position detecting circuit 50, the amount of movement of the blood vessel image Ev' from the one-dimensional reference position is calculated on the basis of the light reception signal of the one-dimensional CCD 42. On the basis of this amount of movement, the galvanometric mirror 22 is driven by the galvanometric mirror control circuit 49, and the received position of the blood vessel image Ev' on the one-dimensional CCD 42 is controlled so as to become constant.

In the present embodiment, the system control means 47 controls the gradation ND filter driving means 66 on the basis of the output of the one-dimensional CCD 42 to thereby control the tracking light so that a blood vessel image Ev' of high contrast may be obtained, but alternatively, the examiner may operate a gradation ND filter operating portion, not shown, in conformity with the blood vessel image Ev' which is the output of the one-dimensional CCD 42 to thereby move the gradation ND filter 65 so as to control the tracking light.

What is claimed is:

1. An eye fundus examining apparatus comprising:
   a first optical system for projecting measurement light onto the fundus of an eye;
   a deflecting member provided in said first optical system for deflecting said measurement light;
   a light receiving element for receiving the measurement light reflected from the fundus of the eye, a predetermined parameter of a target on the fundus of the eye being measured from light reception information of said light receiving element;
   a second optical system for projecting a tracking light beam to an area including said target on the fundus of the eye;
   an image pickup element for receiving the image of said target illuminated by said tracking light beam; and
   a control system for driving said deflecting member and directing said measurement light onto said target so that the distance of deviation from an illuminated point on the eye fundus illuminated by said measurement light under an ideal condition to said target image received on said image pickup element becomes a set value, said set value being suitably resettable.

2. An apparatus according to claim 1, wherein said measurement light and said tracking light beam are separable from each other due to their wavelengths.

3. An apparatus according to claim 1, wherein said control system has a detecting portion for detecting the distance of deviation from a tracking reference position on said image pickup element initially set at the conjugate position of the illuminated point on the eye fundus illuminated by said measurement light under the ideal condition to said target image received by said image pickup element, a directing system for driving said deflecting member so that the distance of deviation becomes zero, and directing said measurement light onto said target image, and tracking reference position correcting means for rendering said tracking reference position suitably movable and resettable.

4. An apparatus according to claim 1, further having changing means for changing the projection angle or the projected position of said measurement light on the incident side of said deflecting means.

5. An eye fundus examining apparatus comprising:
   a light beam scanning system for deflecting a light beam in conformity with a control signal;
   a light source emitting a tracking light beam;
   a tracking light beam applying system for directing the tracking light beam from said light source to a measured portion of an eye to be examined through said light beam scanning system;
   a beam power controlling portion for controlling the beam power of the tracking light beam provided in said tracking light beam applying system;
   an imaging optical system for directing scattered reflected light of said tracking light beam scattered and reflected from the measured portion of the eye to be examined to a light receiving device through said light beam scanning system; and
   a control system for controlling said light beam scanning system in conformity with the output from said light receiving device.

6. An apparatus according to claim 5, wherein said beam power controlling portion has an optical member partially differing in transmittance.

7. An eye fundus examining apparatus comprising:
   a light beam scanning system for deflecting a light beam in conformity with a control signal;
   a light source emitting a tracking light beam;
   a tracking light beam applying system for directing the tracking light beam from said light source to a measured portion of an eye to be examined through said light beam scanning system;
   a beam power controlling portion for controlling the beam power of the tracking light beam provided in said tracking light beam applying system;
   an imaging optical system for directing scattered reflected light of said tracking light beam scattered and reflected from the measured portion of the eye to be examined to a light receiving device through said light beam scanning system; and
   a control system for controlling said light beam scanning system and said beam power controlling portion in conformity with the output from said light receiving device.

8. An apparatus according to claim 7, wherein said beam power controlling portion has an optical member partially differing in transmittance.

* * * * *

UNITED STATES PATENT AND TRADEMARK OFFICE
CERTIFICATE OF CORRECTION

PATENT NO.  : 5,894,337
DATED       : April 13, 1999
INVENTOR(S) : SATORU OKINISHI, ET AL.

It is certified that error appears in the above-identified patent and that said Letters Patent is hereby corrected as shown below:

COLUMN 1

Line 21, "$|\Delta max2||/\cos\beta$" should read --$|\Delta fmax2||/\cos\beta$--.
Line 30, "the" (1st occurrence) should read --this--.
Line 51, "at" should be deleted.

COLUMN 2

Line 56, "are" should read --is--.

Signed and Sealed this

Fourth Day of January, 2000

Attest:

Attesting Officer

Acting Commissioner of Patents and Trademarks